(12) United States Patent
Jin et al.

(10) Patent No.: US 11,448,616 B2
(45) Date of Patent: Sep. 20, 2022

(54) METHOD FOR RELATIVE QUANTITATIVE ANALYSIS OF POLYMER USING MALDI MASS SPECTROMETRY

(71) Applicant: LG CHEM, LTD., Seoul (KR)

(72) Inventors: Kyoungjoo Jin, Daejeon (KR); Yongjin Bae, Daejeon (KR); Young Hee Lim, Daejeon (KR); Yeu Young Youn, Daejeon (KR)

(73) Assignee: LG CHEM, LTD., Seoul (KR)

( * ) Notice: Subject to any disclaimer, the term of this patent is extended or adjusted under 35 U.S.C. 154(b) by 2 days.

(21) Appl. No.: 17/263,822

(22) PCT Filed: Apr. 8, 2020

(86) PCT No.: PCT/KR2020/004713
§ 371 (c)(1),
(2) Date: Jan. 27, 2021

(87) PCT Pub. No.: WO2020/209584
PCT Pub. Date: Oct. 15, 2020

(65) Prior Publication Data
US 2021/0293754 A1   Sep. 23, 2021

(30) Foreign Application Priority Data

Apr. 8, 2019 (KR) .................. 10-2019-0040988
Apr. 7, 2020 (KR) .................. 10-2020-0042122

(51) Int. Cl.
*G01N 27/64* (2006.01)
*G01N 1/28* (2006.01)
(Continued)

(52) U.S. Cl.
CPC .......... *G01N 27/64* (2013.01); *G01N 1/2813* (2013.01); *H01J 49/0418* (2013.01); *H01J 49/164* (2013.01)

(58) Field of Classification Search
CPC ... G01N 27/64; G01N 1/2813; H01J 49/0418; H01J 49/164
See application file for complete search history.

(56) References Cited

U.S. PATENT DOCUMENTS 7,578,206 B2   8/2009   Brock et al.
7,732,378 B2   6/2010   Thompson et al.
(Continued)

FOREIGN PATENT DOCUMENTS

EP     1711819 A1      10/2006
JP     2004-529325 A    9/2004
(Continued)

OTHER PUBLICATIONS

Hsiao, et al.(2001).Analysis of Polymer Additives by Matrix-Assisted Laser Desorption Ionization/Time of Flight Mass Spectrometer Using Delayed Extraction and Collision Induced Dissociation. Journal—Chinese Chemical Society. vol. 28. pp. 1017-1027.
(Continued)

*Primary Examiner* — Nicole M Ippolito
*Assistant Examiner* — Hanway Chang
(74) *Attorney, Agent, or Firm* — Dentons US LLP (57) ABSTRACT

A method for relative quantitative analysis of a polymer using MALDI mass spectrometry, the method comprising the steps of preparing a plurality of polymer specimens having a thickness variation of 30% or less by electrospraying a solution including a polymer sample, a monomeric internal standard material, and a matrix through a mask for each different concentration of the polymer sample; obtaining MALDI mass spectra by irradiating laser beams to each of the plurality of polymer specimens, and calculating a signal intensity ratio of the polymer sample to the small molecule internal standard from peak results of the spectra; and depicting the calculated signal intensity ratio according (Continued)

to the concentration of the polymer sample to prepare a quantitative calibration curve, and the method capable of providing MALDI mass spectra with reduced overlapping peaks and thereby providing the relative quantitative analysis of a polymer with improved accuracy.

15 Claims, 8 Drawing Sheets

(51) Int. Cl.
*H01J 49/04* (2006.01)
*H01J 49/16* (2006.01)

(56) References Cited

U.S. PATENT DOCUMENTS

| | | |
|---|---|---|
| 8,164,051 B2 | 4/2012 | Shiokawa et al. |
| 2016/0172174 A1 | 6/2016 | Takahashi |
| 2020/0219709 A1 | 7/2020 | Bae et al. |

FOREIGN PATENT DOCUMENTS

| | | |
|---|---|---|
| JP | 2005-503557 A | 2/2005 |
| JP | 2007-514173 A | 5/2007 |
| JP | 2009-264950 A | 11/2009 |
| JP | 2016-114400 A | 6/2016 |
| KR | 10-1434092 B1 | 8/2014 |
| KR | 10-2017-0013362 A | 2/2017 |
| KR | 10-2019-0040652 A | 4/2019 |
| KR | 10-2019-0059496 A | 5/2019 |

OTHER PUBLICATIONS

Schwarzinger, et al.(2012). Quantitative Analysis of Polymer Additives With MALDI-TOF MS Using an Internal Standard Approach. J.Am.Soc.Mass Spectrom. vol. 23. pp. 1120-1125.

Choi, et al.(2012). Analysis of Poly(ethylene glycol) Using Matrix-Assisted Laser Desorption/Ionization-Mass Spectrometry: Novel Matrix Systems Using Ultraviolet Light Absorber and Stabilizer. International Journal of Mass Spectrometry. vol. 17-22. pp 328-329.

1) BHB-PPG + PPG sample

2) AP-PDMS + H-PDMS sample

BHB-PPG          PPG

AP(Allylphenol)-PDMS     H-PDMS

METHOD FOR RELATIVE QUANTITATIVE ANALYSIS OF POLYMER USING MALDI MASS SPECTROMETRY

CROSS-REFERENCE TO RELATED APPLICATIONS

This application is a National Stage Application of International Application No. PCT/KR2020/004713, filed on Apr. 8, 2020, which claims the benefit of priorities from Korean Patent Application Nos. 10-2019-0040988, filed on Apr. 8, 2019 and 10-2020-0042122, filed on Apr. 7, 2020, the entire disclosures of which are incorporated by reference herein.

FIELD OF DISCLOSURE

The present disclosure relates to a method for relative quantitative analysis of polymers using MALDI-MS spectrometry, and more specifically to a method of performing relative quantitative analysis using a small molecule compound as an internal standard for polymer specimens having a uniform thickness with various concentrations.

BACKGROUND

MALDI (matrix-assisted laser desorption ionization) is a technique that indirectly ionizes specimens through a matrix, which is easy for mass spectrometry of polymers, but difficult to use for quantitative analysis due to lack of reproducibility of spectrum.

Nevertheless, techniques for quantitative analysis of specimens using MALDI mass spectrometry have been developed. For example, it has been reported that if the spectrum is obtained by maintaining the temperature of the MALDI plume, which is a vapor generated from the specimen by a laser pulse, at a constant level, reproducibility of the spectrum can be secured and quantitative analysis is possible through the preparation of quantitative calibration lines.

Meanwhile, the present inventors have found that the thickness of the polymer specimen is a factor affecting the pattern of the MALDI spectrum, and they have produced a specimen having a uniform thickness by controlling the thickness of the specimen at a constant level through electrospray with applying a mask (Korean patent application No. 10-2017-0130010, filing date: 2017 Oct. 11, Applicant: LG Chem.), they have created a quantitative calibration line using a polymer as an internal standard for the above specimen of uniform thickness (Korean patent application No. 10-2017-0157161, filing date: 2017 Nov. 23, Applicant: LG Chem.), and they have developed a method for performing relative quantitative analysis of polymers by preparing a quantitative calibration line using a matrix signal without separate internal standard (Korean patent application No. 10-2018-0102447, filing date: 2018 Aug. 30, Applicant: LG Chem.). The above patent literatures are incorporated herein by reference in their entity.

However, in the case of using polymers as an internal standard, the mass spectrum is complicated because the molecular weight of the polymer is similar to that of the sample to be analyzed and the accuracy of quantitative analysis can be reduced due to overlapping of the peaks. In addition, in the case of using matrix signals, the accuracy of quantitative analysis can be reduced due to overlapping of matrix peaks and other peaks.

Therefore, there is still a need for a technique to solve the problem of reduction in quantitative accuracy due to peak overlap in the MALDI mass spectrum.

SUMMARY

The problem to be solved by the present disclosure is to provide a method for relative quantitative analysis of polymers that enables to increase the accuracy of quantitative analysis by reducing peak overlap that may occur when using polymer internal standard or matrix signals in the MALDI mass (MALDI-MS) spectrum of the polymer specimen.

According to one aspect of the present disclosure, there is provided a method for relative quantitative analysis of polymers using MALDI-MS spectrometry, comprising:

(S1) preparing a plurality of polymer specimens having a thickness variation of 30% or less by electrospraying a solution containing a polymer sample, a small molecule internal standard and a matrix through a mask for each different concentration of the polymer sample;

(S2) obtaining a MALDI mass spectrum by irradiating a laser to each of the plurality of polymer specimens and calculating signal intensity ratios of the polymer sample and the small molecule internal standard from peak results of the spectrum; and (S3) preparing a quantitative calibration line by plotting the calculated signal intensity ratios according to the concentration of the polymer sample.

The polymer sample may be a polymer having a molecular weight of 1000 Da or more, for example it may comprise poly-(N-β-hydroxyethyl-2,2,6,6-tetramethyl-4-hydroxypiperidyl succinate (Tinuvin 622), 2,2-bis(hydroxymethyl)butyric acid-poly(propylene glycol) (BHB-PPG), allylphenol-polydimethylsiloxane (AP-PDMS), H-polydimethylsiloxane (H-PDMS), or a mixture thereof.

The small molecule internal standard may comprise 2,2'-methylenebis[6-(2H-benzotriazol-2-yl)-4-(1,1,3,3-tetramethylbutyl)phenol, bis(2,2,6,6-tetramethyl-4-piperidyl)sebacate or a mixture thereof.

The step (S1) of preparing the polymer specimens by electrospraying through the mask comprises: (i) providing an electrospray apparatus comprising a sample plate and a main nozzle for electrospray and mounting the mask on the sample plate; and (ii) electrospraying the solution containing a polymer sample, a small molecule internal standard and a matrix by the main nozzle onto the sample plate on which the mask is mounted, wherein the mask may comprise a hole through which the polymer sample solution electrosprayed from the main nozzle can pass onto the sample plate so as to obtain the polymer specimen having a small thickness variation on the sample plate.

The diameter of the hole included in the mask may be 1 to 2 mm. In addition, the material of the mask may be stainless steel or aluminum.

The step (i) of mounting the mask on the sample plate may further comprise adjusting position of the mask in a direction of at least one of x-axis, y-axis, or z-axis.

The electrospray apparatus may further comprise an auxiliary nozzle surrounding and coaxial with the main nozzle, and the step (ii) of electrospraying the polymer sample solution onto the sample plate by the main nozzle may further comprise spraying a solvent from the auxiliary nozzle to prevent the matrix from depositing in the vicinity of the main nozzle.

In addition, the electrospray apparatus may further comprise a sheath gas supply pipe surrounding and coaxial with the auxiliary nozzle, and the step (ii) of electrospraying the polymer sample solution onto the sample plate by the main nozzle may further comprise guiding the solution by jetting a sheath gas from the sheath gas supply pipe so that the solution is sprayed to a predetermined position on the sample plate.

The size of area where the polymer sample solution is electrosprayed on the sample plate may be 40 to 180 $mm^2$, specifically 40 to 80 $mm^2$.

The thickness of the polymer specimen may be in the range of 500 nm to 10 μm.

The thickness variation of the polymer specimen may be 30% or less as measured at three or more spots for the same polymer specimen (spot-to-spot).

A relative standard deviation (RSD) indicating an error of a result of the MALDI mass spectrum measured on the polymer specimen, may be ±15% or less as measured at three or more spots for the same polymer specimen (spot-to-spot).

Advantageous Effect

According to the present disclosure, MALDI mass spectrometry is performed by preparing a uniform polymer specimen having a small thickness variation by electrospray with a mask, wherein a small molecule compound is used as an internal standard. Accordingly, a reproducible MALDI mass spectrum with the reduced peak overlap can be obtained, from which a more accurate relative quantitative analysis of the polymer can be performed.

DETAILED DESCRIPTION

Since various modifications and variations can be made in the present disclosure, particular embodiments are illustrated in the drawings and will be described in detail in the detailed description. It should be understood, however, that the disclosure is not intended to be limited to the particular embodiments, but includes all modifications, equivalents, and alternatives falling within the spirit and scope of the disclosure.

One embodiment of the present disclosure relates to a method for relative quantitative analysis of polymers using MALDI-MS spectrometry, the method comprising (S1) preparing a polymer specimen; (S2) obtaining a MALDI mass spectrum for the polymer specimen and calculating signal intensity ratios from the results; and (S3) preparing a quantitative calibration line using the signal intensity ratios. Hereinafter, specific steps of the method will be described in more detail with reference to the drawings.

Preparation of Polymer Specimen

In the present disclosure, to prepare a polymer specimen for MALDI mass spectrometry, a solution containing a polymer sample, a small molecule internal standard and a matrix is electrosprayed through a mask. A plurality of polymer specimens is prepared with varying concentrations of the polymer sample, wherein the concentration of the small molecule internal standard in each polymer specimen is constant.

In one embodiment of the present disclosure, the polymer sample may be a polymer compound having a molecular weight of 1000 Da or more, such as 3000 to 4000 Da.

Examples of polymer samples applicable in the present disclosure include poly-(N-β-hydroxyethyl-2,2,6,6-tetramethyl-4-hydroxypiperidyl succinate (Tinuvin 622), 2,2-bis (hydroxymethyl)butyric acid-poly(propylene glycol) (BHB-PPG), allylphenol-polydimethylsiloxane (AP-PDMS), H-polydimethylsiloxane (H-PDMS) or a mixture thereof.

The small molecule internal standard is used for relative quantitative analysis of the polymer compounds as described above. Here, "relative quantification" refers to quantification of a polymer sample by adding a certain internal standard with the polymer sample during the preparation of a polymer specimen and determining a relative value of peak result of each sample to peak result of the internal standard.

In the present disclosure, a small molecule compound is used as an internal standard for relative quantitative analysis of such a polymer sample. As the small molecule compound, any compound can be used having signals not overlapped with signals of the matrix and the polymer sample. For example, not only monomers but also oligomers having a molecular weight region different from that of polymer compounds having a high degree of polymerization can be used as the small molecule compound. Since such a small molecule compound has a different molecular weight region from the matrix and the polymer sample, it is possible to reduce the peak overlap that may occur in the MALDI mass spectrum.

In one embodiment of the present disclosure, 2,2'-methylenebis[6-(2H-benzotriazol-2-yl)-4-(1,1,3,3-tetramethyl-butyl)phenol commercially available as Tinuvin 360 or bis(2,2,6,6-tetramethyl-4-piperidinyl)sebacate commercially available as Tinuvin 770 may be used as the small molecule internal standard.

The small molecule internal standard may be added so that the volume ratio of small molecule internal standard to the polymer sample is 1:99 to 99:1. The content is not particularly limited as long as the monomer and the polymer sample having different molecular weight region can be detected together.

In one embodiment of the present disclosure, the matrix used in the preparation of the polymer sample absorbs energy from an energy source such as a laser and transfers the energy to the polymer sample to be analyzed, thereby heating and ionizing the polymer sample.

The matrix is not particularly limited as long as the polymer sample and the small molecule compound used as the internal standard can be detected. Examples thereof include DCTB(trans-2-[3-(4-tert-Butylphenyl)-2-methyl-2-propenylidene]malononitrile), DHB(2,5-dihydroxybenzoic acid), CHCA(α-cyano-hydroxycinnamic acid), SA(sinapic acid, 3,5-dimethoxy-4-hydroxycinnamic acid), and the like.

In addition, the polymer sample, the small molecule internal standard, and the matrix can be used in the form of a solution dissolved in an organic solvent such as tetrahydrofuran (THF), xylene or chloroform, respectively, and the concentration can be appropriately selected. For example, the polymer sample can be used in the specimen to be prepared at various concentrations within the range of 0.1 to 10 mg/ml. In addition, the small molecule internal standard and the matrix may be used for each specimen at a constant concentration of 0.1 mg/ml and 10 mg/ml, respectively, but are not particularly limited thereto.

A polymer specimen for MALDI mass spectrometry may be prepared by applying a solution containing the polymer sample, the small molecule internal standard material and the matrix as described above to a sample plate, for example, a stainless steel plate.

The signal ratio of the sample to the matrix or the internal standard in the MALDI mass spectrum depends on the temperature during the ion production reaction by laser irradiation, so it is necessary to control the temperature of the ion production reaction at a constant level. If the thickness of the polymer specimen to be produced is non-uniform, the temperature may be non-uniform when irradiating a laser to the specimen to cause an ion generation reaction. In this case, it is difficult to obtain a reproducible MALDI mass spectrum.

Figure 1:
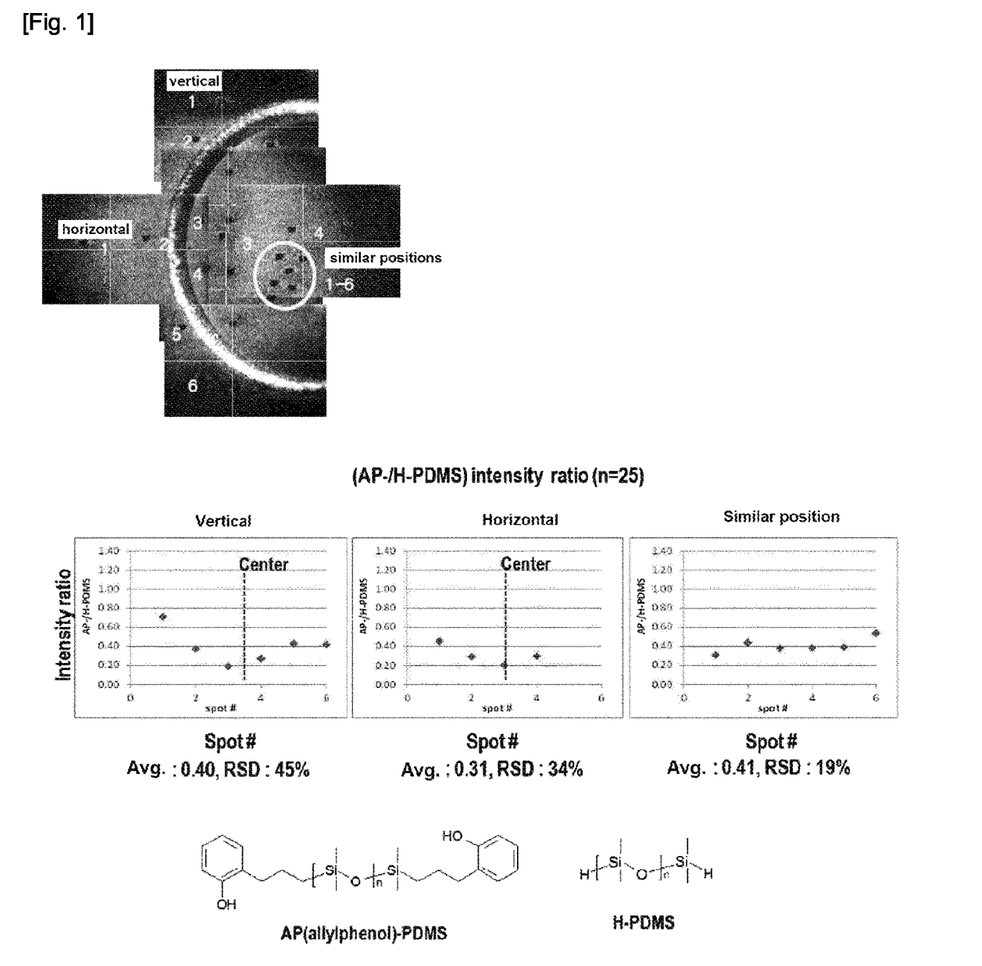
FIG. 1 shows the difference in MALDI mass spectrum depending on the analysis position of the specimen for the specimen prepared from the prior art.

For example, FIG. 1 shows the difference in MALDI mass spectrum depending on the analysis position of the specimen for the specimen prepared from the prior art. It can be found that from the results of MALDI spectra obtained from different positions, the spectrum obtained at the center of the specimen are different from the spectrum obtained at the edge of the specimen. In other words, the spectrum change occurs with a tendency from the center to the edge of the specimen, and the spectra measured at similar positions show a relatively similar tendency.

In MALDI, the spectra tend to coincide with each other when the temperature of the plume which is the vapor generated from the specimen by the laser pulses is the same, but the spectra tend to be different when the temperature of the plume is different. Thus, the result of FIG. 1 means that the temperature of the plume varies depending on the position in the specimen.

In addition, the temperature of the plume is involved in the thickness of the specimen. As the thickness increases, the temperature of the plume tends to increase. Thus, from this general fact, it can be predicted that a factor affecting the MALDI spectrum pattern of polymers is the thickness of the specimen.

Figure 2:
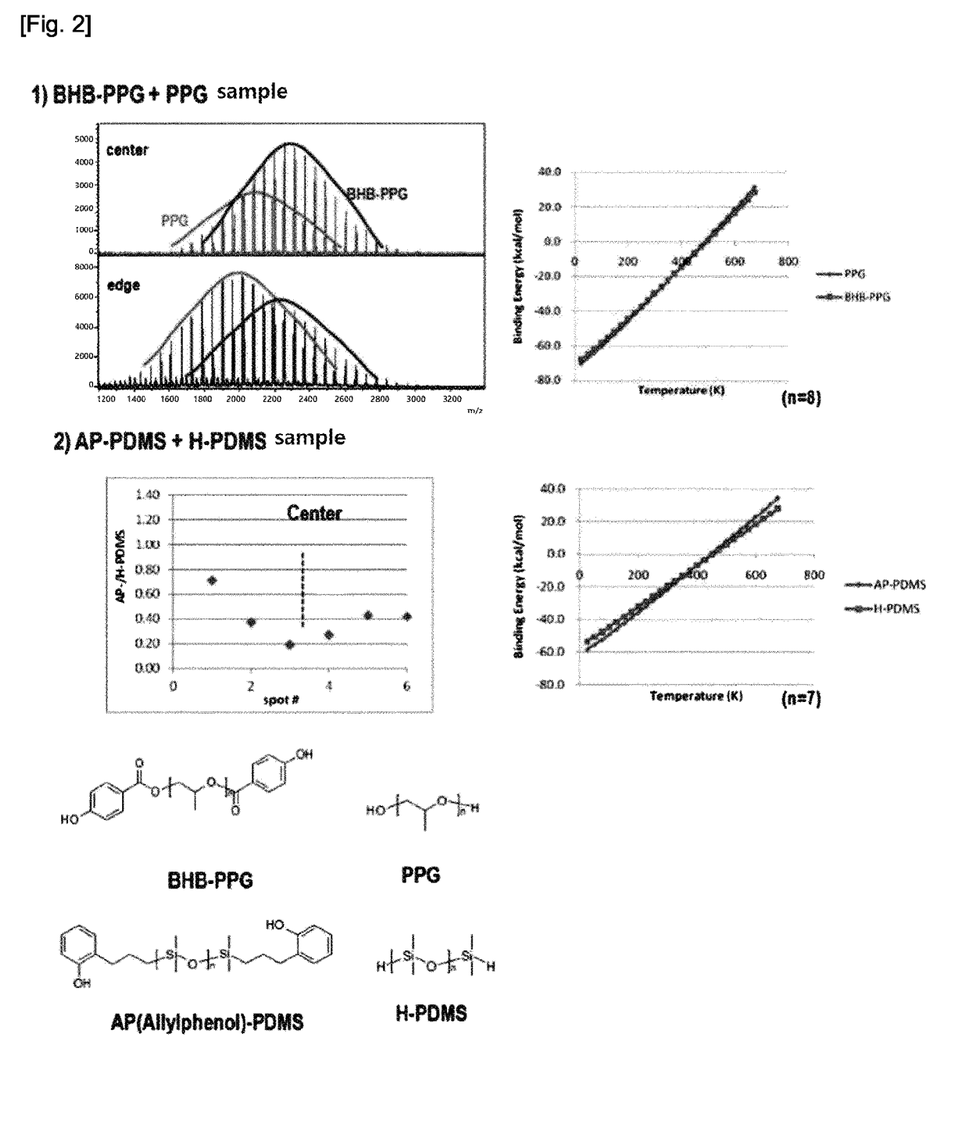
FIG. 2 shows the difference in MALDI mass spectrum depending on the thickness of the specimen and the difference in ionization efficiency depending on the temperature of the plume.

FIG. 2 is a result showing the effect of the temperature change according to the thickness of the specimen on the ionization efficiency of the polymer. From the change in intensity of the spectrum according to the specimen position of the BHB-PPG+PPG sample in FIG. 2(1), it can be seen that the signal intensity ratio of BHB-PPG to PPG is greater in the center than at the edge of the specimen. The cause of this can be predicted from the graph showing a change in Na+ binding energy according to the temperature. FIG. 2 is a graph illustrating a change in Na+ binding energy depending on the temperature. The lower the Na+ binding energy is, the higher the Na+ affinity is. Therefore, it can be predicted that the higher the temperature, the more ions generated by the BHB-PPG than the PPG. In the case of AP-PDMS+H-PDMS sample of FIG. 2(2), the experimental results can be sufficiently predicted by using a graph illustrating a change in Na+ binding energy according to the temperature.

As such, the temperature of the plume affects the ionization efficiency, and fluctuations in the temperature of the plume may result from differences in the specimen thickness, so that the specimen having a uniform thickness should be used in order to obtain a reproducible MALDI spectrum.

Therefore, the present disclosure uses an electrospray method using a mask to control the polymer specimen to have a small thickness variation at a plurality of spots in the manufacture of the polymer specimen, and specifically comprises the following steps:

(i) providing an electrospray apparatus comprising a sample plate and a main nozzle for electrospry and mounting the mask on the sample plate; and (ii) electrospraying the solution containing a polymer sample, a small molecule standard and a matrix (hereinafter referred to as "polymer sample solution" or "sample solution") by the main nozzle onto the sample plate on which the mask is mounted.

The mask may comprise a hole through which the polymer sample solution electrosprayed from the main nozzle can pass onto the sample plate so as to obtain the polymer specimen having a small thickness variation on the sample plate.

The material of the mask is not particularly limited, but may be stainless steel or aluminum. In addition, the shape of the mask may also vary, including a rectangle, a circle, and the like, and the length of one side of the mask may be several cm in size. For example, when the mask has a rectangular shape, the length of one side may be 1 to 4 cm, and when the mask has a circular shape, the diameter may be 1 to 4 cm. In this case, the hole provided in the mask may have a size of, for example, 1 to 2 mm in diameter.

Electrospray through this mask is performed to spread the sample solution around the hole of the mask. For example, the jetting diameter of the sample solution may be 4 to 15 mm and the area in which the sample solution is sprayed may be in the range of 40 to 180 mm$^2$, specifically 40 to 80 mm$^2$. That is, the jetting area of the sample solution for electrospray according to the present disclosure is not limited to the size of the mask hole, but spraying may be carried out widely including the vicinity of the mask hole.

In this manner, the polymer sample solution passing through the hole may be applied on the sample plate with a uniform and thin thickness, and the solution not passing through the hole remains on the mask. If the jetting area is limited to the size of the mask hole, it may be difficult to produce a specimen of uniform thickness.

In one embodiment of the present disclosure, the thickness of the polymer specimen manufactured by the spraying as described above may be 500 nm to 10 μm, such as 0.5 to 5 μm or 1 to 2 μm. When satisfying such a thickness range, it is possible to maintain uniformity to minimize the thickness variation while ensuring a thickness capable of analyzing the polymer sample.

As such, the uniform polymer specimen may be manufactured by selecting only a portion having a small thickness variation from the area where the sample solution is sprayed onto the sample plate.

The electrospray method generally has application to various fields from the viewpoint that the polymer sample can be sprayed and deposited more uniformly over a large area. Electrospray is easy to build a system because of the simple shape and structure of the nozzle and it is very simple to produce droplets from hundreds of nanometers to tens of microns. In addition, since the droplets have a monodisperse distribution and the surface of droplet is charged, there is an advantage that the droplets are hardly to bind to each other and thus easy to be controlled. In addition, it is possible to spray over a large area at atmospheric pressure. Also, it is possible to produce a specimen having more stable characteristics due to the electrostatic effect.

Figure 3:
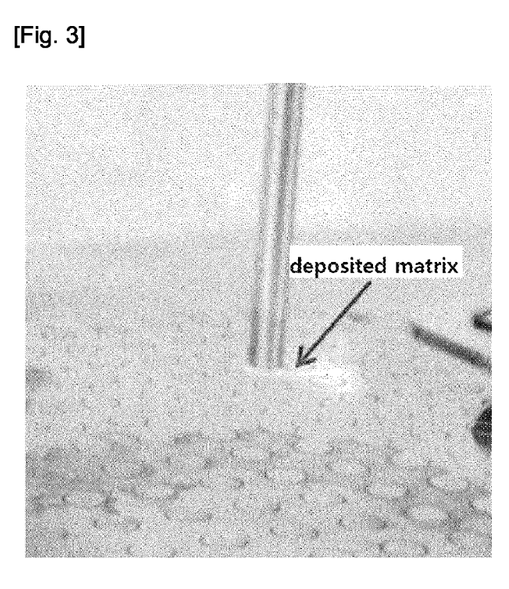
FIG. 3 shows a phenomenon that the matrix is deposited at the tip of the nozzle in the spraying process using the electrospray of the prior art.

However, when spraying a solution containing a polymer sample, a small molecule internal standard and a matrix in a spraying process using a general electrospray, a phenomenon may occur in which the matrix is deposited at the tip of the nozzle (see FIG. 3). Due to the matrix deposited at the tip of the nozzle, there was a problem of the deteriorated reproducibility of the electrospray of the sample. In other words, due to the matrix deposited at the tip of the nozzle, it was difficult for the sample to be sprayed to a predetermined position.

Figure 4A:
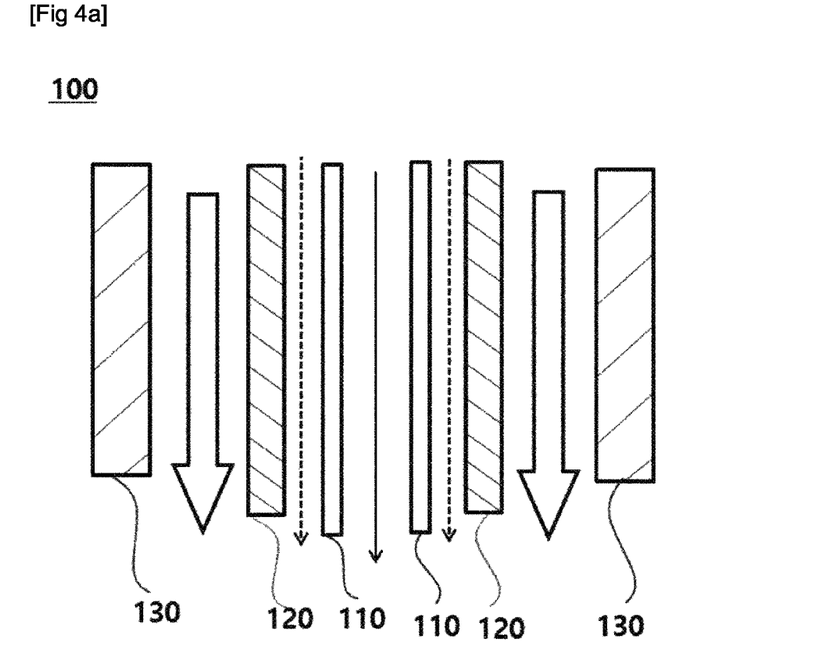
FIGS. 4a to 4d schematically illustrate an electrospray apparatus applied with a mask for manufacturing a polymer specimen according to one embodiment of the present disclosure and an application process thereof.

This problem may be overcome by using an auxiliary nozzle together with the main nozzle. For example, as can be seen in the electrospray apparatus used in the embodiment of the present disclosure of FIGS. 4a to 4d and its application process, the nozzle portion 100 of the electrospray apparatus may comprise a main nozzle 110 for jetting a solution containing a polymer sample, a small molecule internal standard and a matrix, and an auxiliary nozzle 120 surrounding and coaxial with the main nozzle 110, wherein the auxiliary nozzle 120 is adapted to spray a solvent (see FIG. 4a). In FIG. 4a, a solid line arrow in the main nozzle 110 indicates a flow of the polymer sample sprayed from the main nozzle 110, and a dotted line arrow in the auxiliary nozzle 120 indicates a flow of the solvent sprayed from the auxiliary nozzle 120. That is, by additionally spraying the solvent from the auxiliary nozzle 120 surrounding the main nozzle 110 while spraying the polymer sample solution from the main nozzle 110, it is possible to prevent the phenomenon of the deposition of the matrix at the tip of the nozzle, which is a problem in the spraying process using the electrospray according to the prior art, thereby improving the reproducibility of electrospray of the polymer sample. As the solvent to be sprayed through the auxiliary nozzle, tetrahydrofuran (THF) may be used.

In addition, the polymer sample solution electrosprayed from the main nozzle 110 is to be sprayed to a predetermined position. The inlet of the main nozzle 110 may protrude further toward the sample plate than the inlet of the auxiliary nozzle 120. For example, the inlet of the main nozzle 110 may protrude about 1 mm to 2 mm toward the sample plate than the inlet of the auxiliary nozzle 120. The amount of solvent to be sprayed from the auxiliary nozzle 120 may be, for example, 30 to 60% of the amount of solvent sprayed from the main nozzle 110.

Additionally or alternatively, by providing a sheath gas supply pipe 130 surrounding and coaxial with the auxiliary nozzle 120, a sheath gas is also sprayed to around the polymer sample when the polymer sample is sprayed from the main nozzle 110, so that the sheath gas guides the polymer sample to be sprayed to a predetermined position. In FIG. 4a, the thick arrow in the sheath gas supply pipe 130 indicates the sheath gas sprayed from the sheath gas supply pipe 130. Thereby, the reproducibility of the electrospray of the polymer sample can be improved. As the sheath gas, for example, nitrogen gas ($N_2$) may be used. For example, nitrogen gas may be released at 100 to 1000 cc/min, and in one embodiment 1000 cc/min.

As described above, in the present disclosure, while spraying the sample solution comprising the polymer sample, the small molecule internal standard and the matrix from the main nozzle 110, the solvent is sprayed from the auxiliary nozzle 120 surrounding the main nozzle 110 or the sheath gas is sprayed from the sheath gas supply pipe 130 surrounding and coaxial with the auxiliary nozzle 120 to around the sample solution to be sprayed. Accordingly, the sample solution electrosprayed from the main nozzle 110 can be sprayed to a predetermined position on the sample plate.

Figure 4B:
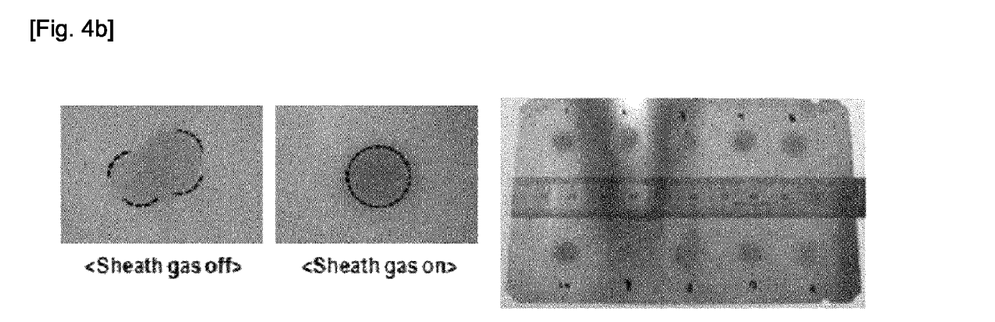

FIG. 4b shows that the sample solution is loaded at a predetermined position when the sheath gas is used. For example, reproducibility was confirmed by repeating electrospray 10 times at 2 cm intervals.

Figure 4C:
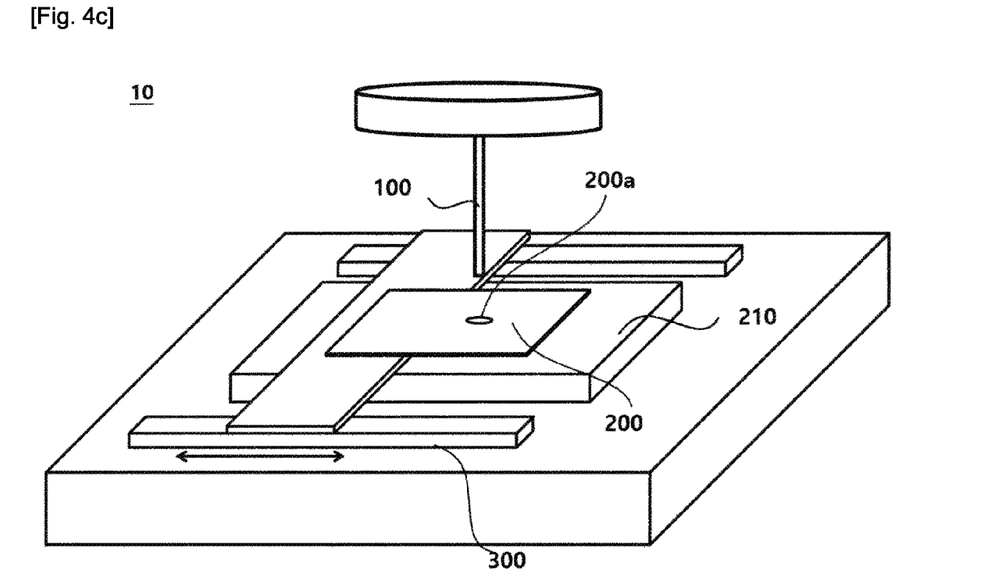

In addition, referring to FIG. 4c, in one embodiment of the present disclosure, the mask position adjusting unit 300 may be used together with the mask 200 in the manufacture of the polymer specimen. That is, when the polymer sample solution is electrosprayed on the sample plate placed on the sample stage 210, the mask 200 is placed on the sample plate for electrospray so that only a portion having a small variation in thickness can be selected as a specimen from the area where the polymer sample is sprayed on the sample plate placed on the sample stage 210. In addition, since the mask 200 is mounted in the mask position adjusting unit 300, the position of the mask 200 on the sample plate may be adjusted by the mask position adjusting unit 300.

The center of the mask 200 comprises a hole 200a that is generally fitted to the size of the specimen corresponding to the portion having the desired thickness variation. Samples that do not pass through the hole 200a among the samples to be electrosprayed remain on the mask 200. When the mask 200 is mounted on the sample plate according to FIG. 4c with the improved reproducibility of the electrospray of the polymer sample as described with reference to FIG. 4a, the polymer sample to be electrosprayed may pass through the hole 200a of the mask 200 and be placed on the sample plate to produce a specimen having a desired thickness variation.

Figure 5:
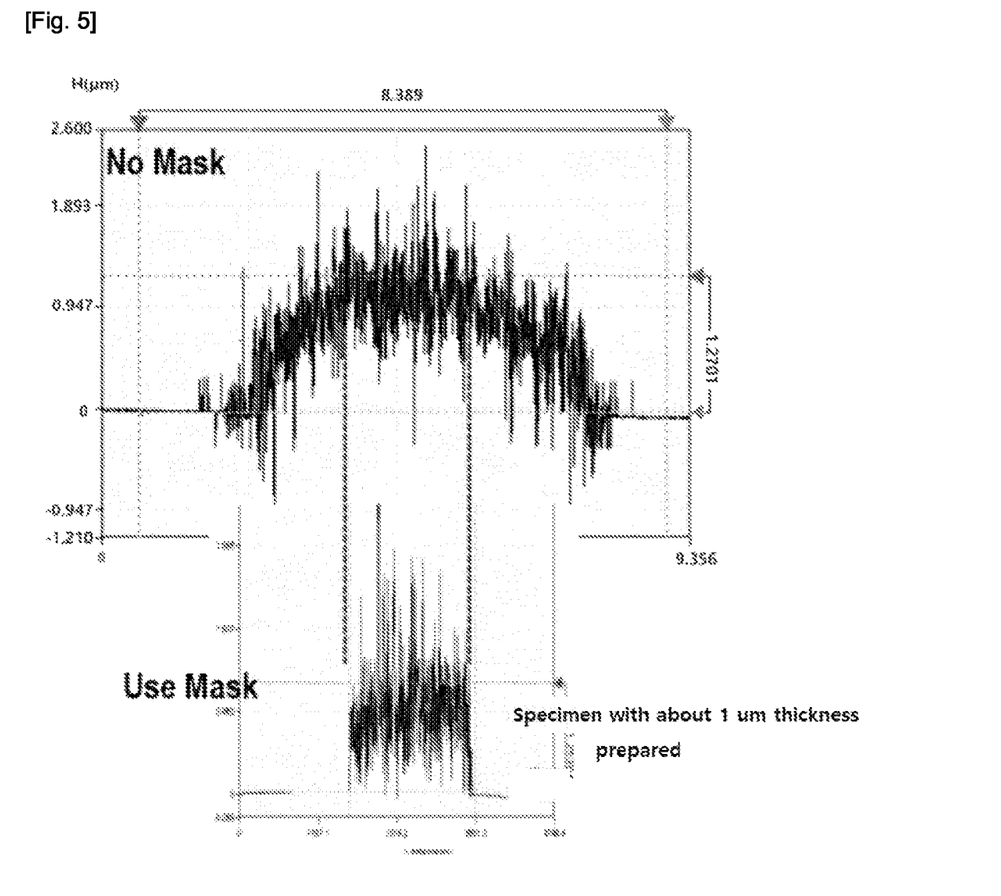
FIG. 5 illustrates a process of manufacturing a specimen having a thickness of 1 μm by selecting a center of the specimen from the wide area sprayed using a mask according to one embodiment of the present disclosure.

FIG. 5 illustrates a process of manufacturing a specimen having a thickness of 1 μm by selecting a center of the specimen from a widely sprayed area using a mask according to an exemplary embodiment of the present disclosure. Through this process, a sample having a thickness variation of 30% or less, for example 25%, finally remains on the sample stage 210.

As described above, the mask 200 may be made of stainless steel, aluminum, or the like and may have a rectangular or circular shape. In addition thereto, various materials and shapes can be applied. For example, when the mask 200 has a rectangular shape, the length of one side may be 1 to 4 cm, and when the mask 200 has a circular shape, the diameter may be 1 to 4 cm. In this case, the diameter of hole 200a may be, for example, 1 to 2 mm.

Figure 4D:
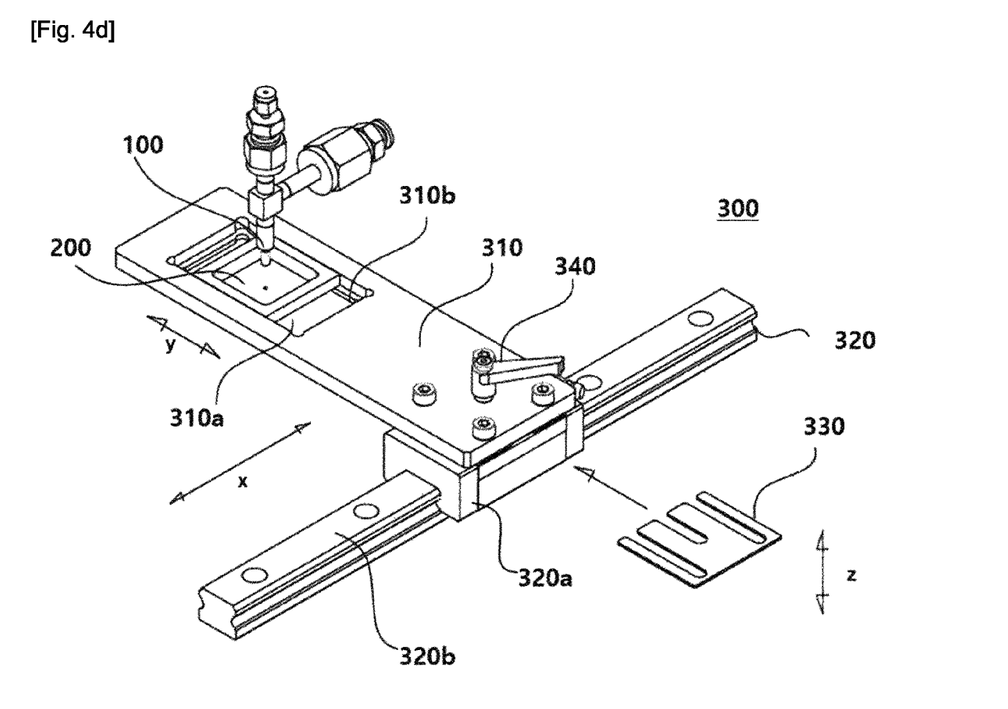

In addition, referring to FIG. 4d, the mask position adjusting unit 300 may comprise a mask holder 310 on which the mask 200 can be mounted.

In one embodiment of the present disclosure, the mask holder 310 may further comprise an opening 310a, in which the mask 200 may be mounted and the mounted mask 200 may move in one axis direction (e.g., y-axis). The opening 310a may have, for example, a rectangular shape and the width of one side of the rectangle of the opening 310a may match the width of the mask 200. The width of the other side of the opening 310a is larger than the width of the mask 200 so that the mask 200 mounted in the opening 310a can be moved and mounted. Both edges of the opening 310a may comprise a convex portion 310b, and thus the mask 200 may be placed on the convex portion 310b of the opening 310a.

The mask position adjusting unit 300 comprises a linear motion rail 320 extending perpendicular to the length direction of the mask holder 310, and the mask holder 310 may be mounted to a mounting portion 320a of the linear motion rail 320. The mask holder 310 is fixed to the mounting portion 320a by, for example, a bolt, and can move on the x-axis on the rail portion 320b of the linear motion rail 320. The rail portion 320b may further comprise a ruler (see FIG. 4d) to display how much the mask holder 310, that is, the mask 300 which is mounted on the mask holder 310 moves on the x-axis.

If the mask holder 310 moves in the x-axis direction on the linear motion rail 320, the mask 300 may move in the y-axis direction within the opening 310a of the mask holder 310, as described above. In addition, the mask position adjusting unit 300 may adjust the height of the mask holder 310 in the z-axis direction (the direction perpendicular to the upper surface of the sample stage 210). As the plate on which the specimen is placed, various plates such as a stainless steel plate and an ITO glass may be used. Therefore, the height (the height in the z-axis) of the mask holder 310, i.e., the height of the mask 300 which is mounted on the mask holder 310 needs to be adjusted according to the height of the plate. When the mask holder 310 is mounted on the mounting portion 320a of the linear motion rail 320, a spacer 330 for adjusting the height of the mask holder 310 may be disposed between the mask holder 310 and the mounting portion 320a. For example, a plurality of spacers may be provided and the number of spacers may be increased from 0 (zero) until the corresponding height is reached. Alternatively, each spacer having a height corresponding to the plate may be provided. The present disclosure is not limited to the above, and various modifications and changes are possible.

In addition, in one embodiment of the present disclosure, the mask position adjusting unit 300 may further comprise a fixing unit 340 for fixing the mask holder 310 onto the linear motion rail 320.

As described above, according to the process for manufacturing the polymer specimen according to the embodiment of the present disclosure, when the polymer sample solution is electrosprayed on the sample plate placed on the sample stage 210, the mask 200 is used as shown in FIGS. 4b to 4c so that only a portion having a small thickness variation of 30% or less can be selected as a specimen from the area where the polymer sample is widely sprayed on the sample plate. In order to adjust the position of the mask 200, the movement in the z-axis direction of the mask holder 310 on which the mask 200 is mounted may be controlled by the spacer 330 between the mask holder 310 and the linear motion rail 320, the movement in the x-axis direction of the mask holder 310 on which the mask 200 is mounted may be controlled by the linear motion rail 320, and the mask 200 may be moved in the y-axis direction within the opening 310a of the mask holder 310. However, the method of adjusting the position of the mask as described above is an embodiment of the method for manufacturing a specimen using the mask of the present disclosure. The present disclosure is not limited to the above, and various modifications and changes are possible with respect to the method of adjusting the position of the mask.

In addition, the electrospray apparatus 10 to be used in one embodiment of the present disclosure may further comprise a sample injection adjusting unit (not shown), and the sample injection adjusting unit may specifically comprises a pump 30a for adjusting the injection amount of the polymer sample supplied to the main nozzle 110 and a pump 30b for adjusting the injection amount of the solvent supplied to the auxiliary nozzle 120. In addition, the amount of the sheath gas supplied to the sheath gas supply pipe 130 may be adjusted by a sheath gas adjusting unit (not shown).

As described above, according to the present disclosure, polymer specimens having a uniform thickness of 30% or less, such as 25% or less can be prepared by electrospray through a mask. The polymer specimens thus prepared can be applied to commercial MALDI-TOF MS equipment to obtain a reproducible MALDI spectrum (with an error of ±30% or less), thereby enabling quantitative analysis of the polymer sample.

Acquisition of MALDI Mass Spectrum and Calculation of Signal Intensity Ratio

The MALDI mass spectrum is obtained by irradiating a laser to each of the plurality of polymer specimens having a small thickness variation, and signal intensity ratios of the polymer sample to the matrix or signal intensity ratios of the polymer sample to the internal standard are calculated from the peak results of the spectrum.

The laser is a means for applying energy to the polymer specimen, and in particular, it may be a nitrogen laser or Nd: YAG laser.

When irradiating the laser to the specimen, a plurality of ion spectra may be obtained by irradiating several times to a single spot of the specimen, or irradiating to a plurality of spots of the specimen. For example, in order to obtain a spectrum having a good S/N ratio (signal-to-noise ratio), the MALDI mass spectrum may be obtained for several spots, for example 20 to 80 spots at 50 to 2000 shots per spot of the specimen to determine an average value. In addition, experiments may be performed 3 times or more on the specimens with the same condition.

The MALDI mass spectrum obtained by the above process may have a value of RSD (relative standard deviation) indicating an error of ±30% or less. For example, a reproducible MALDI mass spectrum can be obtained in which an error may be ±15% or less when measured for three or more spots on the same specimen (spot-to-spot) and an error may be ±30% or less even when measured for three or more specimens manufactured under the same conditions (sample-to-sample).

The ions appearing in the MALDI mass spectrum are for a protonated polymer sample, a protonated matrix, a protonated internal standard and fragment products generated in the ion source. Therefore, the peak pattern of the MALDI mass spectrum is determined by the number of ions, the signal ratio and the like.

When the polymer is used as an internal standard, the MALDI mass spectrum may be complicated and peak overlap may occur. In the present disclosure, the peak overlap can be reduced by using a small molecule as an internal standard.

As described above, in the present disclosure, after obtaining the MALDI mass spectrum with the reduced peak overlap, signal intensity ratios of the polymer sample and the small molecule internal standard are calculated therefrom, thereby improving the accuracy of quantitative analysis.

Preparation of Quantitative Calibration Line

In order to quantify the polymer using the MALDI mass spectrum obtained for the polymer specimen according to the present disclosure, a quantitative calibration line is prepared by plotting the signal intensity ratios of the polymer sample and the small molecule internal standard as calculated above according to the concentration of the polymer sample.

Figure 7:
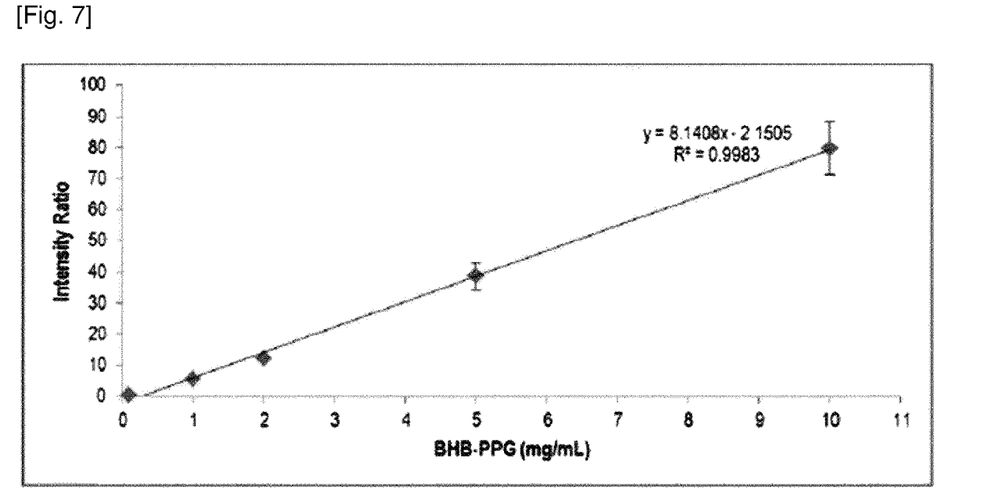
FIG. 7 shows a quantitative calibration line prepared by plotting signal intensity ratios of the polymer sample and the small molecule internal standard according to Example of the present disclosure according to various concentrations.

According to an embodiment of the present disclosure, the calibration line prepared by plotting the signal intensity ratios of the polymer sample and the small molecule internal standard according to the concentration of the polymer sample are all linear ($R^2$=0.98 or more, see FIG. 7).

In addition, the RSD (relative standard deviation) of each point in the calibration curve according to the present disclosure may be ±12% or less.

Hereinafter, embodiments of the present disclosure will be described in detail so that those skilled in the art can easily carry out the present disclosure. The present disclosure may, however, be embodied in many different forms and should not be construed as limited to the embodiments set forth herein.

EXAMPLE

Step 1: Preparation of Polymer Specimen

A solution having BHB-PPG as a polymer to be analyzed dissolved in THF (tetrahydrofuran) was prepared at a concentration of 0.1 mg/ml, 1 mg/ml, 2 mg/ml, 5 mg/ml and 10 mg/ml. A solution of Tinuvin 360 in THF (0.1 mg/ml) as a small molecule internal standard, and a solution of DCTB (trans-2-[3-(4-tert-butylphenyl)-2-methyl-2-propenylidene] malononitrile) in THF (10 mg/ml) as matrix, and NaTFA solution (0.02 M, in THF) were prepared.

The matrix solution, NaTFA solution, polymer solution and small molecule internal standard were mixed in 9/1/0.5/0.5 (v/v/v/v), wherein the polymer compound solution was used at each concentration to obtain a plurality of polymer sample solutions.

The plurality of polymer sample solutions prepared above were electrosprayed using the electrospray apparatus 10 and the mask 200 having a hole with a diameter of 2 mm in FIG. 4c, respectively, to prepare a plurality of polymer specimens.

Specifically, the polymer sample was electrosprayed for 10 minutes at a flow rate of 0.5 μL/min (1st flow) on a stainless steel plate, and the thickness of the electrosprayed specimen was measured. However, the stainless steel plate has a rough surface such that it is not suitable to measure the thickness of the specimen. Therefore, in order to measure the thickness of the electrosprayed specimen, the polymer sample solution was again electrosprayed for 10 minutes at a flow rate of 0.5 μL/min (1st flow) on an ITO glass, and then the thickness of the specimen was measured at 2 μm interval using an optical profiler. The average thickness for the measured thickness profiles was about 1 μm (see FIG. 5).

In addition, assuming that the spot size of the MALDI laser is 50 μm, the standard deviation of the average of the 25 measured values was measured, and the resulting thickness variation was about 25%.

Step 2: Acquisition of MALDI Mass Spectrum and Calculation of Signal Intensity Ratio Using a MALDI-TOF mass spectrometer (UltrafleXtreme, Bruker Daltonics, Germany), MALDI mass spectrometry was performed by irradiating with 337 nm nitrogen laser (MNL100, Lasertechnik Berlin, Berlin, Germany) to 400 spots at 500 shots per spot for each polymer specimen manufactured in the step 1.

Such mass spectrometry was performed in triplicate for each polymer specimen (i.e., for each concentration of the polymer sample) to obtain a MALDI mass spectrum. Subsequently, the signal intensity ratios of the polymer sample (BHB-PPG) and the small molecule internal standard (Tinuvin 360) were calculated and averaged.

Figure 6:
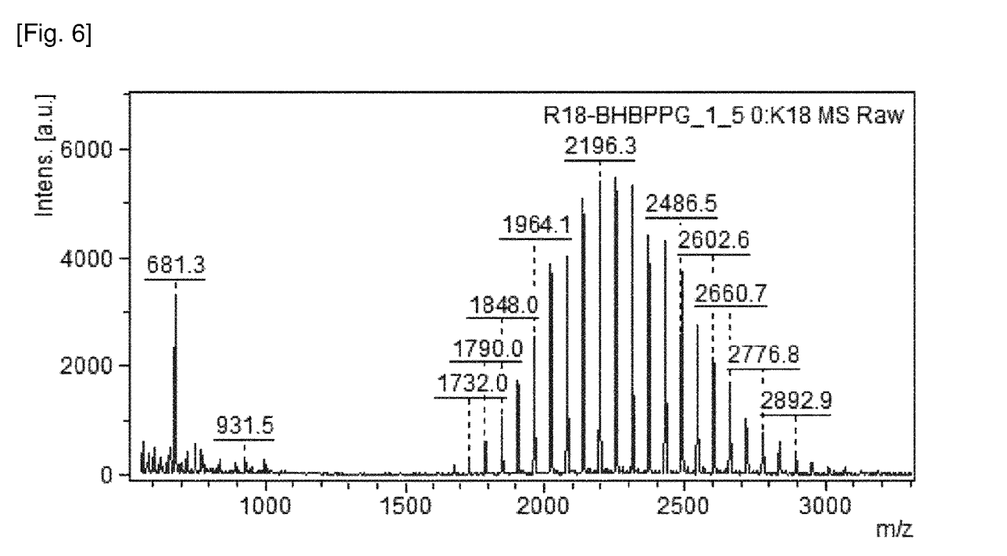
FIG. 6 shows a data acquisition process from MALDI mass spectrum obtained for the specimen manufactured according to one embodiment of the disclosure.

FIG. 6 shows a result of MALDI mass spectrum obtained for the polymer specimen manufactured according to one embodiment of the disclosure.

In FIG. 6, the monomer peak of Tinuvin 360 used as an internal standard corresponds to m/z 681.3, and the peaks of BHB-PPG, a polymer sample to be analyzed, correspond to the range of m/z 1700 to 3000. That is, as Tinuvin 360 and BHB-PPG had different molecular weight region each other, peak overlap did not occur in the spectrum, from which it is possible to improve accuracy in the quantitative analysis of BHB-PPG.

Step 3: Preparation of Quantitative Calibration Line

The signal intensity ratios of BHB-PPG and Tinuvin 360 calculated in step 2 were plotted according to the concentration of BHB-PPG to prepare a calibration line, and the results are shown in FIG. 7.

As can be seen from FIG. 7, after performing MALDI on a homogeneous polymer specimen having a small thickness variation of 25% and using signals of BHB-PPG and Tinuvin 360 from the spectrum obtained therefrom, a linear calibration line ($R^2$=0.98 or more) with RSD (relative standard deviation) of 12% or less at each point was obtained.

Comparative Example

The same procedure as in Example 1 was performed, except that Tinuvin 622, a polymer was used as the internal standard in the step 1 of Example 1.

Figure 8:
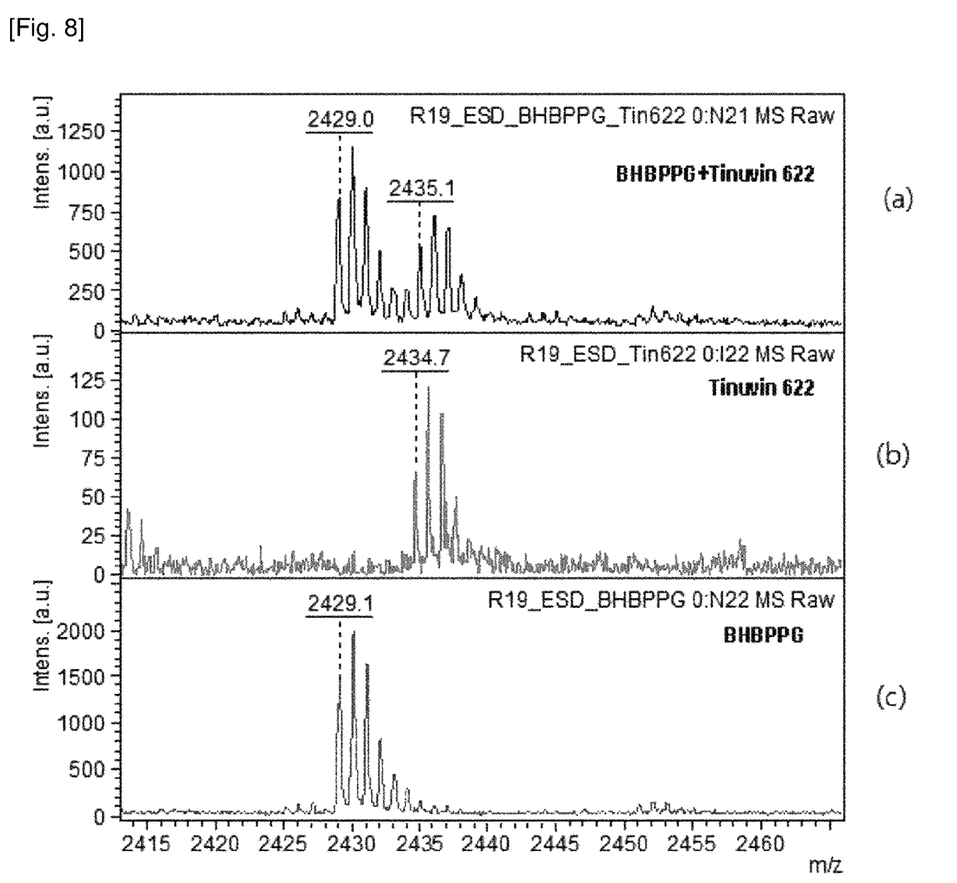
FIG. 8 shows a result of the MALDI mass spectrum obtained for the polymer specimen prepared in Comparative Example.

FIG. 8 shows a result of the MALDI mass spectrum obtained for the polymer specimen prepared in Comparative Example. FIG. 8(a) is a combination of the peak (b) of the polymer Tinuvin 622 which is an internal standard and the peak (c) of the BHB-PPG which is a polymer sample to be analyzed. As a result, it is found that the spectrum was complicated due to overlapping of peaks occurring as the molecular weight regions of the polymer sample and the polymeric internal standard were similar. In this case, accuracy is deteriorated in quantitative analysis of the polymer sample.

What is claimed is:

1. A method for relative quantitative analysis of a polymer using matrix-assisted laser desorption ionization (MALDI) mass spectrometry, comprising:
   (S1) preparing a plurality of polymer specimens having a thickness variation of 30% or less by electrospraying a solution containing a polymer sample, a small molecule internal standard and a matrix through a mask for each different concentration of the polymer sample;
   (S2) obtaining a MALDI mass spectrum by irradiating a laser to each of the plurality of polymer specimens and calculating signal intensity ratios of the polymer sample and the small molecule internal standard from peak results of the spectrum; and
   (S3) preparing a quantitative calibration line by plotting the calculated signal intensity ratios according to the concentration of the polymer sample.

2. The method according to claim 1, wherein the polymer sample comprises a polymer having a molecular weight of 1000 Da or more.

3. The method according to claim 2, wherein the polymer sample comprises poly-(N-β-hydroxyethyl-2,2,6,6-tetramethyl-4-hydroxypiperidyl succinate (Tinuvin 622), 2,2-bis(hydroxymethyl)butyric acid-poly(propylene glycol) (BHB-PPG), allylphenol-polydimethylsiloxane (AP-PDMS), H-polydimethylsiloxane (H-PDMS), or a mixture thereof.

4. The method according to claim 1, wherein the small molecule internal standard comprises 2,2'-methylenebis[6-(2H-benzotriazol-2-yl)-4-(1,1,3,3-tetramethylbutyl)phenol, bis(2,2,6,6-tetramethyl-4-piperidyl)sebacate or a mixture thereof.

5. The method according to claim 1, wherein the step (S1) of preparing the polymer specimens by electrospraying through the mask comprises:
   (i) providing an electrospray apparatus comprising a sample plate and a main nozzle for electrospray, and mounting the mask on the sample plate; and
   (ii) electrospraying the solution containing a polymer sample, a small molecule internal standard and a matrix by the main nozzle onto the sample plate on which the mask is mounted,
   wherein the mask comprises a hole through which the polymer sample solution electrosprayed from the main nozzle onto the sample plate so as to obtain the polymer specimen having a small thickness variation on the sample plate.

6. The method according to claim 5, wherein the hole included in the mask has a diameter of 1 to 2 mm.

7. The method according to claim 5, wherein the material of the mask is stainless steel or aluminum.

8. The method according to claim 5, wherein the step (i) of mounting the mask on the sample plate further comprises adjusting position of the mask in a direction of at least one of x-axis, y-axis, or z-axis.

9. The method according to claim 5, wherein the electrospray apparatus further comprises an auxiliary nozzle surrounding and coaxial with the main nozzle, and the step (ii) of electrospraying the polymer sample solution onto the sample plate by the main nozzle further comprises spraying a solvent from the auxiliary nozzle to prevent the matrix from depositing in the vicinity of the main nozzle.

10. The method according to claim 5, wherein the electrospray apparatus further comprises a sheath gas supply pipe surrounding and coaxial with the auxiliary nozzle, and the step (ii) of electrospraying the polymer sample solution onto the sample plate by the main nozzle further comprises guiding the solution by jetting a sheath gas from the sheath gas supply pipe so that the solution is sprayed to a predetermined position on the sample plate.

11. The method according to claim 5, wherein size of the area where the polymer sample solution is electrosprayed on the sample plate is 40 to 180 $mm^2$.

12. The method according to claim 11, wherein the size of the area where the polymer sample solution is electrosprayed on the sample plate is 40 to 80 $mm^2$.

13. The method according to claim 1, wherein the polymer specimen has a thickness in the range of 500 nm to 10 μm.

14. The method according to claim 1, wherein the thickness variation of the polymer specimen is 30% or less as measured at three or more spots for the same polymer specimen (spot-to-spot).

15. The method according to claim 1, wherein a relative standard deviation (RSD) indicating an error of a result of the MALDI mass spectrum measured on the polymer specimen, is ±15% or less as measured at three or more spots for the same polymer specimen (spot-to-spot).

* * * * *